(12) United States Patent
Dirauf et al.

(10) Patent No.: US 9,785,131 B2
(45) Date of Patent: Oct. 10, 2017

(54) DEVICE AND METHOD FOR CONTACTLESS CONTROL OF A PATIENT TABLE

(71) Applicant: Siemens Aktiengesellschaft, Munich (DE)

(72) Inventors: Franz Dirauf, Ebensfeld (DE); Sultan Haider, Erlangen (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 271 days.

(21) Appl. No.: 14/706,201

(22) Filed: May 7, 2015

(65) Prior Publication Data

US 2015/0320367 A1    Nov. 12, 2015

(30) Foreign Application Priority Data

May 7, 2014   (DE) ........................ 10 2014 208 540

(51) Int. Cl.
| | |
|---|---|
| *A61B 6/04* | (2006.01) |
| *G05B 15/02* | (2006.01) |
| *A61G 13/02* | (2006.01) |
| *A61B 5/00* | (2006.01) |
| *A61B 34/00* | (2016.01) |

(52) U.S. Cl.
CPC .............. *G05B 15/02* (2013.01); *A61B 5/704* (2013.01); *A61B 6/0407* (2013.01); *A61G 13/02* (2013.01); *A61B 34/25* (2016.02); *A61G 2203/12* (2013.01); *A61G 2210/50* (2013.01)

(58) Field of Classification Search
CPC ....... G05B 15/02; A61B 5/704; A61B 6/0407; A61B 34/25; G06F 3/017; A61G 13/02; A61G 2203/12; A61G 2210/50
See application file for complete search history.

(56) References Cited

U.S. PATENT DOCUMENTS

| | | | | |
|---|---|---|---|---|
| 4,538,289 A | * | 8/1985 | Scheibengraber | ..... A61B 6/032 378/20 |
| 5,005,230 A | * | 4/1991 | Congdon | ............... A61G 13/00 5/308 |
| 5,327,474 A | | 7/1994 | Inoue et al. | |
| 5,636,259 A | * | 6/1997 | Khutoryansky | ......... A61B 6/00 378/196 |
| 5,820,553 A | * | 10/1998 | Hughes | .................... A61B 6/08 378/65 |
| 5,832,056 A | * | 11/1998 | Mochitate | ............ A61B 6/0457 378/195 |
| 5,966,763 A | * | 10/1999 | Thomas | ............... A47C 27/086 5/421 |

(Continued)

FOREIGN PATENT DOCUMENTS

| | | |
|---|---|---|
| CN | 1931094 A | 3/2007 |
| CN | 202151380 U | 2/2012 |

(Continued)

*Primary Examiner* — Ramesh Patel
(74) *Attorney, Agent, or Firm* — Schiff Hardin LLP

(57) ABSTRACT

The invention relates to a device for contact-free control of a patient table includes a camera system for detecting at least one gesture of a user of the device, a processing unit for converting the at least one detected gesture into at least one command for controlling the patient table, and an execution unit for executing the at least one command for controlling the patient table. The device can furthermore include a monitoring system for monitoring the control of the patient table and an authentication system for authenticating the user.

16 Claims, 1 Drawing Sheet

(56) References Cited

U.S. PATENT DOCUMENTS

| | | | | |
|---|---|---|---|---|
| 6,027,247 A * | 2/2000 | Tachi | ............... | A61B 6/0457 |
| | | | | 378/177 |
| 6,031,888 A * | 2/2000 | Ivan | ............... | A61B 6/4464 |
| | | | | 378/196 |
| 6,075,837 A * | 6/2000 | Roos | ............... | A61B 6/4233 |
| | | | | 378/62 |
| 6,431,751 B1 * | 8/2002 | Everett | ............ | A61B 6/4233 |
| | | | | 378/193 |
| 6,897,780 B2 * | 5/2005 | Ulrich | ............ | G06F 19/3418 |
| | | | | 340/286.02 |
| 7,596,205 B2 * | 9/2009 | Zhang | ............ | A61B 6/032 |
| | | | | 378/196 |
| 7,794,145 B2 * | 9/2010 | Xu | ............... | A61B 6/04 |
| | | | | 378/209 |
| 7,828,481 B2 * | 11/2010 | Ye | ............... | A61B 6/0457 |
| | | | | 378/117 |
| 2003/0060808 A1 * | 3/2003 | Wilk | ............ | A61G 3/001 |
| | | | | 606/1 |
| 2004/0076262 A1 | 4/2004 | Shao et al. | | |
| 2004/0193413 A1 * | 9/2004 | Wilson | ............ | G06F 3/017 |
| | | | | 704/243 |
| 2005/0238141 A1 | 10/2005 | Tsujii | | |
| 2011/0118877 A1 | 5/2011 | Hwang et al. | | |
| 2013/0281818 A1 * | 10/2013 | Vija | ............ | A61B 6/467 |
| | | | | 600/407 |
| 2014/0013417 A1 | 1/2014 | Sakai et al. | | |

FOREIGN PATENT DOCUMENTS

| | | |
|---|---|---|
| DE | 102012213426 A1 | 6/2014 |
| KR | 20110057978 A | 6/2011 |
| KR | 20130095663 A | 8/2013 |

\* cited by examiner

DEVICE AND METHOD FOR CONTACTLESS CONTROL OF A PATIENT TABLE

BACKGROUND OF THE INVENTION

Field of the Invention

The present invention relates to a device, a method, and a computer-readable storage medium for contact-free control of a patient table.

Description of the Prior Art

In hospitals it is necessary to transport patients inside various examination devices or between locations and examination rooms. Because of the health status of the patient the patient is frequently transported lying on a patient table. Typically, for an examination with an examination apparatus (e.g. magnetic resonance apparatus, computed tomography apparatus, X-ray apparatus, radiotherapy apparatus, etc.), the patient has to be transported from a location to a place provided for the examination process, usually inside the examination device.

SUMMARY OF THE INVENTION

An object of the present invention is to provide assistance for operating personnel while patients are being transported.

This object is achieved in accordance with the invention in a device for contact-free control of a patient table, the device having a camera system that detects at least one gesture of a user of the device, a processing unit that converts the at least one detected gesture into at least one command for controlling the patient table, and an execution unit that executes the at least one command so as to control the patient table according to the at least one command.

The camera system includes at least one camera, with which a gesture of a user is detected. The camera system can further optionally include a depth sensor, a microphone and/or software, which can be used to assist with detection of the gesture. The use of several cameras for a more exact determination of three-dimensional coordinates is also possible. Examples of suitable camera systems include, but are not limited to, Kinect systems, Time-of-Flight systems, Eye-Toy systems, Move systems, and other machine vision systems designed to detect movement for the purpose of identifying a movement in a detection area of an optical detector.

The processing unit includes at least one computer processor and that converts the at least one detected gesture into at least one command for controlling the patient table.

The execution unit likewise includes at least one computer processor and executes the at least one command for controlling the patient table. The processor of the execution unit can be formed by the processor of the processing unit, and vice versa, but the execution unit is preferably attached to the patient table.

The invention uses the generation of at least one command produced by a gesture of a user in order to enable contact-free control of a patient table. This saves time, since the user does not need to exert force in order to move the patient table, and it satisfies stringent hygiene requirements, since by avoiding contact with the patient table, the table cannot come into contact with any contaminating substances. The patient table can be moved in a horizontal direction and a vertical direction, and can be designed to dock with a medical device or a medical procedure, so that that patient table is fixed to the medical device in order to make it easier for the patient to be moved to another bed, and it can be moved into, out of and inside the medical device. If the patient table is a multipart patient table, the control of the patient table includes the control of the individual parts of the patient table.

The gesture can be a movement of a hand of the user in a particular direction in which the patient table is also to be moved, but may also be the execution of a particular shape that corresponds to a movement of the patient table in a particular direction.

In a preferred embodiment the inventive device includes the patient table. With an integrated device of this type, the operation of the overall system is particularly facilitated.

In another embodiment, the inventive device includes a monitoring system that monitors the control of the patient table. Such a monitoring system can be, for example, a user interface, on which a user can observe the movement of the patient table. Thus, for example, the user can identify incorrect operation of the control and correct a movement of the patient table. This improves the safety of the patient on the patient table and the safety of the overall system.

In another embodiment the monitoring system includes a projection unit that is designed to transmit a position of the controlled patient table. By projecting the position of the patient table, it is particularly easy to monitor the control procedure.

In a preferred embodiment, the device further includes an authentication system for authenticating the user. Authenticating a user as used herein means activating the inventive device for a user, so that the inventive camera system, the inventive processing unit and the inventive execution unit are coordinated with the user. This can be implemented, for example, using stored user profiles. In this manner the inventive device is calibrated to a particular user and thus reacts with increased sensitivity compared to a universal controller without such a calibration.

In another embodiment the authentication system is designed for automatic authentication by means of optical markers. Automatic detection of the user facilitates a changeover of users. Furthermore, the necessity for manual user interaction is thereby obviated. The inventive solution is thus efficient and time-saving and furthermore satisfies stringent hygiene requirements.

In another embodiment, the optical marker is designed as an accessory for the user. An accessory should here for example be understood as an armband, a ring, a plastic card or a similar accessory, which can be worn and/or carried around particularly easily by a user and with which the user can authenticate himself to the authentication system. This ensures a particularly simple type of user identification.

In a preferred embodiment, the authentication system is designed to use gestures made by the user for authentication purposes. An additional gesture-based user identification within the gesture-based device facilitates intuitive use of the overall system. Here too the contact-free user identification satisfies stringent hygiene requirements.

In another embodiment, the authentication system is designed to use chip cards for authentication purposes. Authentication by means of chip cards can take place in addition to authentication by means of optical markers, in that a particular authentication is necessary after a changeover of users, but it can also take place instead of authentication by means of optical markers, in that the changeover of users is triggered only by means of a chip card. Authentication by means of chip cards is a particularly secure variant of authentication, since different methods of encryption can be integrated into the chip cards.

In another embodiment, the camera system is oriented to a position of the user after the user has been authenticated. By identifying a user by means of the authentication system the camera system can also be oriented to a default position associated with the user. This makes it possible to set user preferences and thus saves time if the camera system does not have to be oriented manually to a preferred starting position. Preferably the orientation of the camera system to a position of the user entails parts of the camera system that are not required being switched off and on. Thus an optional depth sensor can for example be associated with a user, another camera can be switched on, and so on. This increases the individuality of the user guidance and equally saves time.

In a preferred embodiment the patient table and the camera system are located in different rooms. This means it is not necessary for the user to be located in a room containing the patient table, and the patient table can be controlled remotely. This approach avoids long paths between patient table and user if the user and the patient are situated at different locations and if when the patient table is moved the user has to locate the patient. This furthermore saves both time and costs. Preferably the device has a second camera for this purpose, for monitoring the patient table.

In the context of the present invention, a method for contact-free control of a patient table is also provided.

This method includes the following steps of detecting at least one gesture of a user with a camera system, in a processor, converting the at least one detected gesture into at least one command for controlling the patient table, and executing the at least one command to control the patient table with an execution unit.

Further, the present invention encompasses a non-transitory, computer-readable data storage medium encoded with programming instructions, which can be loaded in a memory of a programmable controller or computer of a device that operates a patient table. The programming instructions cause the computer to execute, all or some of the previously described embodiments of the inventive method when run in the controller or control computer. In such cases the instructions require program means, e.g. libraries and auxiliary functions, in order to realize the corresponding embodiments of the method. The instructions may be in source code, which must still be compiled or which only has to be interpreted, or in an executable software code, which is to be loaded for execution purposes into the computing unit.

The electronically readable storage medium can be, e.g. a DVD, a magnetic tape or a USB stick, on which electronically readable control information, in particular software, is stored.

The advantages of the inventive method, and the inventive electronically readable storage medium essentially correspond to the advantages of the inventive device, which are explained above in detail. Features, advantages or alternative embodiments mentioned herein are likewise applicable to the other subject matters and vice versa. The corresponding functional features of the method are embodied by corresponding object modules, in particular by hardware modules.

DESCRIPTION OF THE PREFERRED EMBODIMENTS

Figure 1:
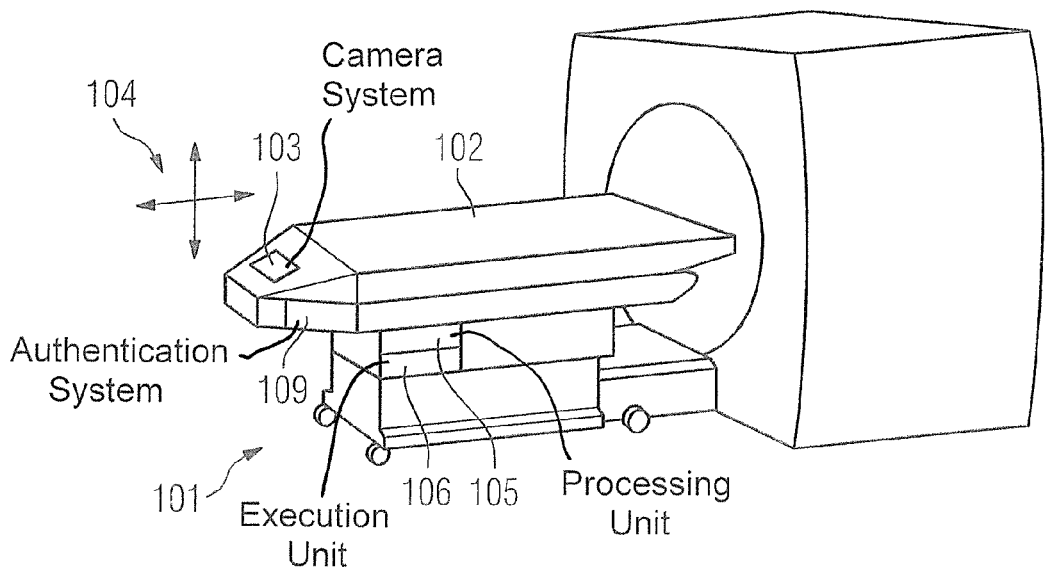
FIG. 1 shows an inventive device for contact-free control of a patient table.

FIG. 1 shows an inventive device 101 for contact-free control of a patient table 102.

The device 101 includes a camera system 103 for detecting at least one gesture 104 of a user 112 of the device 101, a processing unit 105 for converting the at least one detected gesture 104 into at least one command for controlling the patient table 102, and an execution unit 106 for executing the at least one command for controlling the patient table 102.

Figure 2:
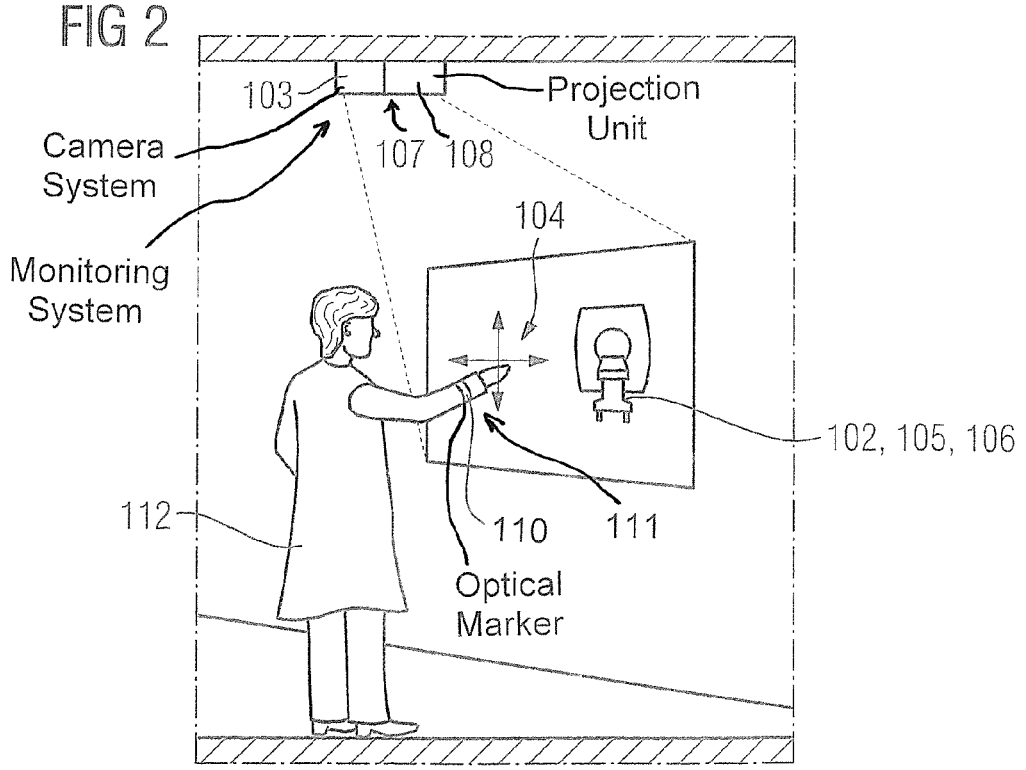
FIG. 2 shows an embodiment of an inventive method for contact-free control of a patient table.

The camera system 103 can be integrated into the patient table 102, as shown in FIG. 1. Alternatively, as shown in FIG. 2, the camera system 3 can be a component of a monitoring system 107 for monitoring the control of the patient table 102, that also includes a projection unit 108, which is designed to project an image showing the position of the controlled patient table 102. An authentication system 109 for authenticating the user 112 also can be integrated in the patient table 102 (in the embodiment of FIG. 1).

The camera system 103 includes at least one camera, with which a gesture 104 of a user 112 can be detected. The camera system 103 can further optionally have a depth sensor, a microphone and/or software, which furthermore can be used to assist with detection of the gesture. The use of several cameras for the more exact determination of three-dimensional coordinates is also possible. Examples of suitable camera systems include, but are not limited to, Kinect systems, Time-of-Flight systems, Eye-Toy systems, Move systems, and other machine vision systems designed to detect movement, which aim to identify a movement in a detection area of an optical detector.

The processing unit 105 has at least one computer processor and is used to convert the at least one detected gesture 104 into at least one command for controlling the patient table 102.

The execution unit 106 likewise has at least one computer processor and is used to execute the at least one command for controlling the patient table 102. The computer processor of the execution unit 106 can in this case also be formed by the computer processor of the processing unit 105, and vice versa. However, the execution unit 106 is advantageously attached to the patient table 102.

In this case a gesture 104 of the user 112, which was detected previously by the camera system 103, generates at least one command to control the patient table 102. The command is executed by the execution unit 106, which is designed for the actual control of the patient table 102. Thus the patient table 102 is controlled by a user 112 without direct contact.

In this case the patient table 102 can be moved in a horizontal and vertical direction, and it can be designed to dock with a medical device or a medical procedure, i.e. so that that the patient table 102 is fixed to the medical device in order thereby to make it easier for the patient to be moved to another bed, and it can be moved into, out of and inside the medical device. If the patient table 102 is a multipart patient table, the control of the patient table 102 embodies control of the individual parts of the patient table 102.

Using the monitoring system 107, for example a user interface, a user 112 can observe the movement of the patient table 102, and using the projection unit 108, which is designed to transmit a position of the controlled patient table 102, the user 112 can detect, for example, incorrect operation of the control and correct a movement of the patient table 102.

Using the authentication system 109 the inventive device 101 can be calibrated to a particular user 112. Authenticating a user 112 as used herein means activating the inventive device 101 by the user 112, so that the inventive camera system 103, the inventive processing unit 105 and the inventive execution unit are coordinated with the user. This can be implemented, for example, using stored user profiles.

FIG. 2 shows an embodiment of an inventive method for contact-free control of a patient table 102.

In this case a user 112 generates a gesture 104 that is detected by the camera system 103 and generates at least one command to control the patient table 102. The command is executed by the execution unit 106, which is designed for the actual control of the patient table 102. The patient table 102 is controlled by the user 112 without direct contact.

The method thus the following steps: detecting at least one gesture 104 of a user 112 by means of a camera system 103, converting the at least one detected gesture 104 into at least one command for controlling the patient table 102 by means of a processing unit 105, and executing the at least one command to control the patient table 102 by means of an execution unit 106.

The gesture 104 can be a movement of a hand of the user 112 in a particular direction in which the patient table 102 is also to be moved, but it may also be an execution of a particular shape which corresponds to a movement of the patient table 102 in a particular direction.

The method optionally includes authentication of the user 112, which in the embodiment of FIG. 2 takes place by the use of an optical marker 110, which is designed as an accessory 111, in this case as an armband, for the user 112.

During execution of the method, the authentication system 109 identifies the user on the basis of the optical marker 110 and, for example, activates the user's user profile. Furthermore, after authentication of the user 112 the camera system 103 can be oriented to a position of the user 112. Preferably the orientation of the camera system 103 to a position of the user 112 entails parts of the camera system 103 that are not required being displayed or not.

Alternative and/or additional variants for authenticating a user 112 are authentication by means of gestures 104 of the user 112, and/or authentication by means of chip cards.

Furthermore, it is possible for the patient table 102 and the camera system 103 to be located in different rooms, and the patient table 102 can therefore be controlled remotely. To this end a second camera can be used for device monitoring.

To summarize, the invention relates to a device for contact-free control of a patient table, that includes a camera system for detecting at least one gesture of a user of the device, a processing unit for converting the at least one detected gesture into at least one command for controlling the patient table, and an execution unit for executing the at least one command for controlling the patient table.

In an advantageous embodiment the device includes a monitoring system for monitoring the control of the patient table and an authentication system for authenticating the user.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for contact-free control of a patient table that is movably mounted on a table base so as to be movable relative to a patient receiving opening of a medical examination apparatus, said device, comprising:
    a camera that detects at least one gesture made by a person that corresponds in direction or shape to a desired movement of said patient table relative to said opening, and that converts said gesture into image data that represents said at least one gesture;
    a computer processor in communication with said camera that receives said image data from said camera and is configured to convert said image data representing said at least one gesture into at least command for controlling movement of the patient table;
    an execution unit in communication with said computer processor that is provided with said command and that is configured to generate and emit a control signal to execute said at least one command that produces a movement of the patient table, relative to said patient-receiving opening, corresponding to said at least one command; and
    a monitoring system comprising a projector configured to project, at a projection site within a field of view of said person, a projected image of said patient table executing said movement, and thereby allowing said person to alter said movement executed by said table, if said movement executed by said table does not correspond to said desired movement, by making another gesture that is detected by said camera and converted into further image data that are converted into at least one further command provided to said execution unit, which alters said movement of said patient table.

2. A device as claimed in claim 1 comprising an authentication system configured to authenticate the person making such at least one gesture.

3. A device as claimed in claim 2 wherein said authentication system is configured to automatically authenticate said person by at least one optical marker associated with said person.

4. A device as claimed in claim 3 wherein said optical marker is an accessory worn by said person.

5. A device as claimed in claim 2 wherein said authentication system is configured to authenticate said person by detecting an authentication gesture made by said person.

6. A device as claimed in claim 2 wherein said authentication system is configured to authenticate said person by reading a chip card associated with said person.

7. A device as claimed in claim 2 wherein said authentication system is configured, after authenticating said person, is configured to orient said camera to a location of said person.

8. A device as claimed in claim 1 wherein said patient table and said camera is situated in a different room from the patient table.

9. A device as claimed in claim 1 wherein said camera is integrated into the patient table.

10. A device as claimed in claim 1 wherein said camera is situated remotely from the patient table, as a component of a monitoring system that monitors control of the patient table by the execution unit.

11. A device as claimed in claim 10 wherein said monitoring system comprises a projector that projects an image that designates a position of the patient table.

12. A method for contact-free control of a patient table that is movably mounted on a table base so as to be movable relative to a patient receiving opening of a medical examination apparatus, said device, comprising:
    operating a camera to detect at least one gesture made by a person that corresponds in direction or shape to a desired movement of said patient table relative to said opening and converting said gesture into image data that represents said at least one gesture;
    providing said image data to a computer processor in communication with said camera and, in said computer processor, converting said image data representing said at least one gesture into at least command for controlling a patient table;

in an execution unit in communication with said computer processor that is provided with said command, generating and emitting a control signal that causes said at least one command to be executed by producing a movement of the patient table relative to said patient-receiving opening corresponding to said at least one command; and with a projector, projecting, at a projection site within a field of view of said person, a projected image of said patient table executing said movement, and thereby allowing said person to alter said movement executed by said table, if said movement executed by said table does not correspond to said desired movement, by making another gesture that is detected by said camera and converted into further image data that are converted into at least one further command provided to said execution unit, which alters said movement of said patient table.

13. A method as claimed in claim 12 comprising authenticating said person via an authentication unit.

14. A method as claimed in claim 12 comprising monitoring control of said patient table via a monitoring unit that is situated remotely from said patient table.

15. A method as claimed in claim 12 comprising integrating said camera into said patient table.

16. A non-transitory, computer-readable data storage medium encoded with programming instructions, said storage medium being loaded into a control computer for contact-free control of a patient table that is movably mounted on a table base so as to be movable relative to a patient receiving opening of a medical examination apparatus, said device, said programming instructions causing said control computer to:

operate a camera to detect at least one gesture made by a person that corresponds in direction or shape to a desired movement of said patient table relative to said opening and convert said gesture into image data that represents said at least one gesture;

convert said image data representing said at least one gesture into at least command for controlling a patient table;

operate an execution unit according to said command so as to generate and emit a control signal that executes said at least one command by producing a movement of the patient table relative to said patient-receiving opening corresponding to said at least one command; and operate a projector in order to project, at a projection site within a field of view of said person, a projected image of said patient table executing said movement, and thereby allowing said person to alter said movement executed by said table, if said movement executed by said table does not correspond to said desired movement, by making another gesture that is detected by said camera and converted into further image data that are converted into at least one further command provided to said execution unit, which alters said movement of said patient table.

\* \* \* \* \*